United States Patent [19]

Mittelmeier et al.

[11] Patent Number: 5,049,157
[45] Date of Patent: Sep. 17, 1991

[54] REINFORCED BONE CEMENT

[75] Inventors: Heinz Mittelmeier, Homburg-Schwarzenbach, Fed. Rep. of Germany; Heinz Moser, Selzach; Beat Leu, Ipsach, both of Switzerland

[73] Assignee: Osteo AG, Selzach, Switzerland

[21] Appl. No.: 84,168

[22] Filed: Aug. 12, 1987

Related U.S. Application Data

[63] Continuation of Ser. No. 576,767, Feb. 2, 1984, abandoned, which is a continuation of Ser. No. 430,714, Sep. 30, 1982, abandoned, which is a continuation-in-part of Ser. No. 397,370, Jul. 12, 1982, abandoned, which is a continuation of Ser. No. 48,451, Jun. 14, 1979, abandoned.

[30] Foreign Application Priority Data

Jun. 29, 1978 [EP] European Pat. Off. ........ 78810005.5

[51] Int. Cl.$^5$ ................................. A61F 2/02
[52] U.S. Cl. ......................... 623/16; 523/105
[58] Field of Search ............... 623/16, 18–23; 523/105; 524/533; 128/92 R, 92 VP; 606/86

[56] References Cited

U.S. PATENT DOCUMENTS

| | | | |
|---|---|---|---|
| 3,789,029 | 1/1974 | Hodosh | 623/16 |
| 3,924,274 | 12/1975 | Heimke et al. | 623/18 |
| 4,051,598 | 10/1977 | Sneer | 128/92 R |
| 4,064,566 | 12/1977 | Fletcher et al. | 623/16 |
| 4,064,567 | 12/1977 | Burstein et al. | 623/18 |
| 4,065,817 | 1/1978 | Branemark et al. | 623/18 |
| 4,146,936 | 3/1979 | Aoyagi et al. | 623/18 |
| 4,192,021 | 3/1980 | Deibig et al. | 623/16 |
| 4,451,235 | 5/1984 | Okuda et al. | 433/201.1 |

FOREIGN PATENT DOCUMENTS 7287 1/1980 European Pat. Off. .
53-110999 9/1978 Japan .

OTHER PUBLICATIONS

Hackh's Chemical Dictionary, p. 55, McGraw Hill Inc., 1969.
American Heritage Dictionary, p. 118, Houghton Mifflin Co., 1982.
Klein et al, "Biodegradation Behavior of Various Calcium Phosphate Materials in Bone Tissue", Journal of Biomedical Materials Research, vol. 17, 1983.

Primary Examiner—Karen M. Hastings
Attorney, Agent, or Firm—Marks Murase & White

[57] ABSTRACT

A bone cement exhibiting superior mechanical strength and body compatibility, as well as shortened polymerization time and reduced peak polymerization temperature, includes a conventional polymethyl methacrylate bone cement to which has been added up to about 4% by weight of carbon fibers and from about 1 to about 30% by weight of the mineral components of natural bone tissue (apatite).

7 Claims, 2 Drawing Sheets

REINFORCED BONE CEMENT

This application is a continuation of application Ser. No. 576,767, filed Feb. 2, 1984, now abandoned which is a continuation of Ser. No. 430,714 filed Sept. 30, 1982, now abandoned which is a continuation-in-part of Ser. No. 397,370 filed July 12, 1982, now abandoned, which is a continuation of Ser. No. 48,451 filed June 14, 1979 now abandoned.

BACKGROUND OF THE INVENTION

1. Field of the Invention

The present invention relates to a bone cement formed of homopolymerizable plastics materials, particularly polymethyl methacrylate and its derivatives.

2. Description of the Prior Art

Since about 1960, it has been known to secure endoprostheses, particularly joint prostheses in bones, by means of homopolymerizable bone cements which are polymerized in situ. Polymethyl methacrylate has been widely used as the major constituent of such bone cement. These conventional polymethyl methacrylate cements generally comprise a methyl methacrylate homopolymer or copolymer in combination with a biocompatible reactive monomer such as methyl methacrylate. The systems may also comprise polymerization initiators and cross-linking agents. Such materials are well known in the art and need not be described in detail herein.

The cement is charged into the body aperture while it is still in its plastic polymerization phase. In this phase, it adapts ideally both to the prostheses parts and to the roughness of the bone. At the end of the polymerization phase, the bone cement sets and secure mechanical locking of the prosthesis body in the bone tissue occurs by means of the cement jacket. The bone cement also has a low modulus of elasticity which has the advantage that deformations and relative movement between the prosthesis and the bone tissue occurring when the prosthesis is used are reduced. Nevertheless, in the course of time, aseptic slackening of the prosthesis occurs, which is brought about by a number of factors. Insufficient mechanical strength of the bone cement is one factor, as is insufficient fatigue stability of the cement. Yet another factor is bone resorption caused by the body's reaction to chemical toxic foreign bodies. These foreign bodies are residual monomers and oligomers present in the polymethyl methacrylate cement system.

There have been attempts to increase the mechanical strength of the bond formed by a polymethyl methacrylate bone cement, for example, by inserting a woven basket at the prosthesis-to-bone interface, as described in the U.S. Pat. No. 4,064,567 to Burstein et al. The woven basket disclosed in this patent is formed from material which is compatible with body tissue and is described as interwoven metal wire in the form of an open screen structure. Among the metals disclosed as being suitable for the basket material are titanium, stainless steel, and chrome-cobalt. This patent discloses that plastics and carbon are also contemplated for use as the woven basket material.

Another technique for improving the mechanical strength of a polymerizable bone cement is to uniformly disperse short, high modulus graphite fibers into the cement, as described in U.S. Pat. No. 4,064,566 t Fletcher et al. While the procedure taught by this patent may improve bond strength, it gives rise to several disadvantages. For example, although this patent discloses the use of cements having from 2 to 12% by weight of graphite fibers, use of the preferred amount of fibers, i.e., about 10%, results in a curing time of about one hour. Such a long polymerization time involves unduly long operation times and exposure to infection, however, because an incision cannot be closed until after the bone cement has hardened. This problem is compounded in the case of a total prosthesis implant since it would be necessary to wait until the bone cement has hardened at the cup as well as at the shaft, thus prolonging an operation by as much as two hours merely waiting for the cement to harden. At lower graphite fiber contents, for example, at about 4%, the polymerization time is shortened considerably, but the peak polymerization temperature is increased above the critical temperature of 56° C, known as the protein-denaturation temperature. Accordingly, the use of a bone cement containing 4% graphite fibers will result in heat damage to the environment tissue, accompanied by atrophy and resorption of the bone which leads to slackening of the prosthesis.

While the mechanical strength of a bone-to-prosthesis bond increases with the insertion of a woven basket or graphite fibers in the bone cement, the problems of bone resorption caused by the body's reaction to chemical toxic foreign bodies remains. To solve this particular problem the German Offenlegungsschrift No. 25 02 884 proposes to admix with the bone cement resorbable material such as collagen fibers or bands or cancellous parts. This material is slowly absorbed by the bone, and new bone tissue is built in its place. Other patents disclosing the addition of resorbable material in bone replacements, prosthesis anchoring materials, plastic bone compositions, dental implants or the like include U.S. Pat. Nos. 4,192,021, to Deibig et al, 3,789,029 to Hodosh and 4,051,598 to Sneer. In each of these patents, the disclosed system involves the continuous exchange of resorbable material with new bone tissue. However, the adjunction of said material, alone, will not result in the desired degree of mechanical strength.

SUMMARY OF THE INVENTION

It is therefore an object of the present invention to provide a polymethyl methacrylate-type bone cement which has increased mechanical strength as well as improved body compatibility compared with known bone cements of the type set forth above.

It is also an object of this invention to provide a bone cement which is adapted to be polymerized in situ in an acceptably short period of time and which will exhibit a peak polymerization temperature below the protein-denaturation temperature.

These and other objects and advantages are attained by providing a bone cement which comprises both carbon fibers and non-absorbable mineral components in fine-grain particle form admixed therewith to obtain a honeycomb-like structure, wherein the non-absorbable mineral components include the mineral components of natural bone tissue (apatite) in an amount of between 1 and 30% by weight and the carbon fibers are present in an amount of from about 1 to about 4% by weight.

In a preferred embodiment, the fibers are structured by a linking method such as weaving, knitting or cross-linking by adhesion, and are provided in the form of a tube or stocking and expediently distributed in the cement.

BRIEF DESCRIPTION OF THE DRAWINGS

The invention will be further described by way of example, with reference, to the accompanying drawings, wherein.

DESCRIPTION OF THE PREFERRED EMBODIMENT

As previously mentioned, if the mechanical strength of the bone cement is too low, fracture or connecting tissue separation of the bone tissue from the bone cement may occur. It is therefore necessary to seek to reinforce the bone cement by finding a fiber reinforcement therefore, the fibers being made of a material having a high modulus of elasticity, a high resistance to elongation, perfect adhesion to the bone cement and, above all, a physical compatibility with body tissue. These sought properties are contained, in combination, to a great degree in carbon fibers, which fibers come in a variety of forms.

It is, for example, possible to provide carbon fibers in the form of a powder or particles, or in the form of a fiber fleece, to be fabricated as a cloth-like layer and wetted with bone cement and to wrap the prosthesis part therein. Alternatively, the prosthesis part may be enveloped with a viscous plastics material, and then a carbon fiber wick or a suitably shaped carbon fiber fleece wrapped around it.

Figure 1:
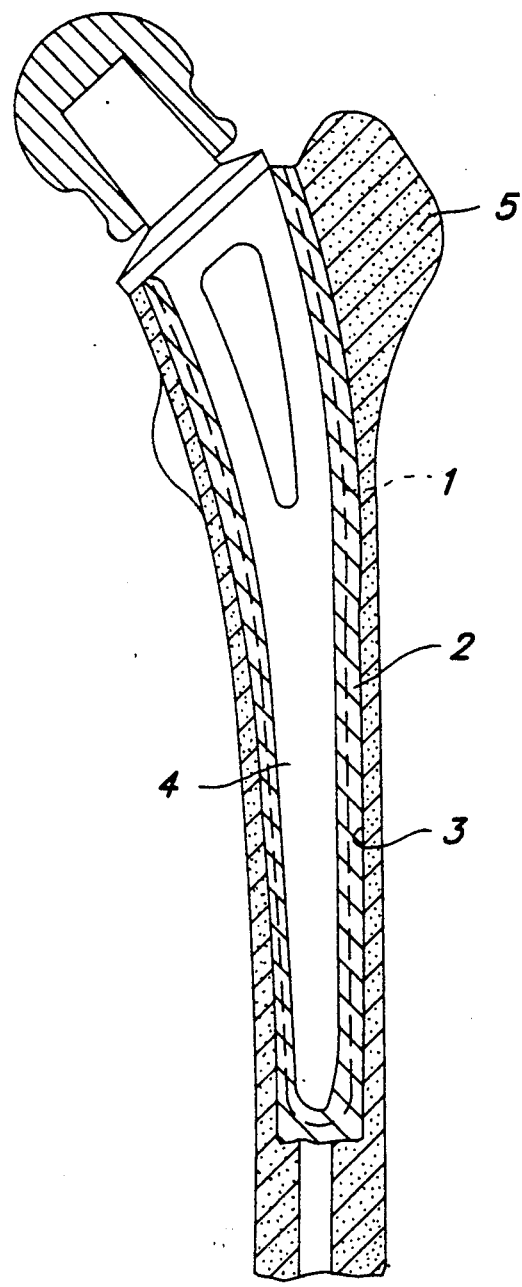
FIG. 1 is a cross-sectional view of a hip joint prosthesis cemented in position in a human femur, the prosthesis having a carbon fiber stocking.

In a preferred embodiment, the fiber material is provided with a preselected aforesaid structure, which structure is made in tubular form cut to size for immediate use or rolled for cutting to size as and when required. This tube, at its lowermost end, may be closed in a stocking-like manner with a thread or the like, or may be manufactured as a stocking which is closed at the bottom, as is shown in FIG. 1. In FIG. 1 there is shown a carbon fiber stocking 1 which is saturated with a conventional polymerizable cement 2 comprised of polymethyl methacrylate and a reactive monomer such as methyl methacrylate. The stocking and cement are accommodated in the narrow cavity 3 of a thigh-bone 5. The prosthesis shaft is designated by the reference numeral 4. Since the cement casing around the prosthesis stem is subjected to compressional and tensional forces and to shear and torsional stresses, a structure is provided, by a suitable method of linking or connecting such as knitting, weaving or cross-linking by adhesion, in which fibers are arranged in the longitudinal, transverse and diagonal directions and in which a plurality of cross-linked layers may be provided one above the other. In this manner, optimal distribution of the fibers is obtained and a closed cement layer is formed which, when the prosthesis shaft is introduced therein, does not separate; thus, the formation of a possible fracture point is successfully avoided.

A known method for producing carbon fibers is to pyrolize acrylic fibers. It is therefore possible to knit, weave or cement the stocking or tube from acrylic fibers and to subsequently pyrolize the stocking or tube. It is also possible to produce the stocking or tube directly from carbon fibers. The thickness of the carbon fibers usually lies within the region of 6 to 15 $\mu$m. In certain cases, it may be expedient to apply the carbon fiber sock or stocking directly to the prosthesis stem, so that the prosthesis part can be sold with this layer provided thereon.

The chemically-toxic foreign body reaction due to the emission of residual monomers and oligomers causes a defined foreign body reaction in the body tissue, as evidenced by rejection cells and connective tissue. As a result, this prevents any direct chemical connection from being formed between the bone and the prosthesis with its cement covering. Thus, the prosthesis is only mechanically anchored which, as experience has shown, frequently fails in the course of time. Consequently, a slackening of the prosthesis often occurs which causes considerable trouble and ultimately necessitates removal of the prosthesis, thereby leaving behind a considerable and often painful defect. It would appear that, in the body environment, aging of the cement occurs, accompanied by decomposition of the polymer chains and reduction of the initial degree of strength of the cement.

In order to further increase the mechanical strength, particularly the stress limit, and to improve the body compatibility, possibly to such an extent that the bone knits with the surface of the cement, the bone cement is mixed with from about 1 to about 30% by weight of a non-resorbable or non-absorbable material such as the mineral components of natural bone tissue, apatite, in particle form. Chemically, apatite is $Ca_5(PO_4)_3(OH)$, which is significantly different from the resorbable tri- and tetra-calcium phosphate materials disclosed in the Deibig et al patent mentioned above. It also differs from the graded bone disclosed in the above-mentioned Hodosh patent which comprises the resorbable collagen part of the bone. It differs, also, from the ground total bone substance disclosed in the above-mentioned Sneer patent, which includes the resorbable collagen part of the bone in addition to the apatite portion.

It is significant to add the apatite in fine-grained form in order to obtain a honeycomb-like structure in the cement. The bone, itself, is a bonding material between the collagen fiber structures and fine-grained apatite. Moreover, in material technology, honeycomb-like structures are used both to save materials and to improve strength. A coarse porosity does not, therefore, appear to be particularly useful since it leads to a reduction in strength. Since apatite does not form chemical bonds with the cement, no reduction of strength occurs in the cement due to chemical effects. The adding of apatite almost certainly causes apatite particles to be located on the contact surface of the cement/apatite mixture with the bone tissue. In this manner, the surface toxicity of the bone cement is reduced. Moreover, the bone in this region may form a bond with the apatite particles which improves the securing of the prosthesis to the bone.

Other important and unexpected advantages resulting from the addition of carbon fibers and apatite in the ranges disclosed herein are a shortening of the polymerization time and a simultaneous lowering of the peak polymerization temperature. This synergistic effect is illustrated schematically in FIG. 2, wherein the characteristics of the bone cements marked A through D may be tabulated as follows:

TABLE

| | Composition: | | | |
|---|---|---|---|---|
| | A | B | C | D |
| Resin Portion of Bone Cement: | Polymethyl Methacrylate | Polymethyl Methacrylate | Polymethyl Methacrylate | Polymethyl Methacrylate |
| Carbon Fibers, % by Weight: | 4 | — | 4 | 10 |
| Apatite, % by Weight: | — | — | 20 | — |
| Approximate Peak Polymerization Temperature, °C.: | 60 | 57 | ·54 | 50 |
| Polymerization Time: | Acceptable | Acceptable | Acceptable | Not acceptable |

Figure 2:
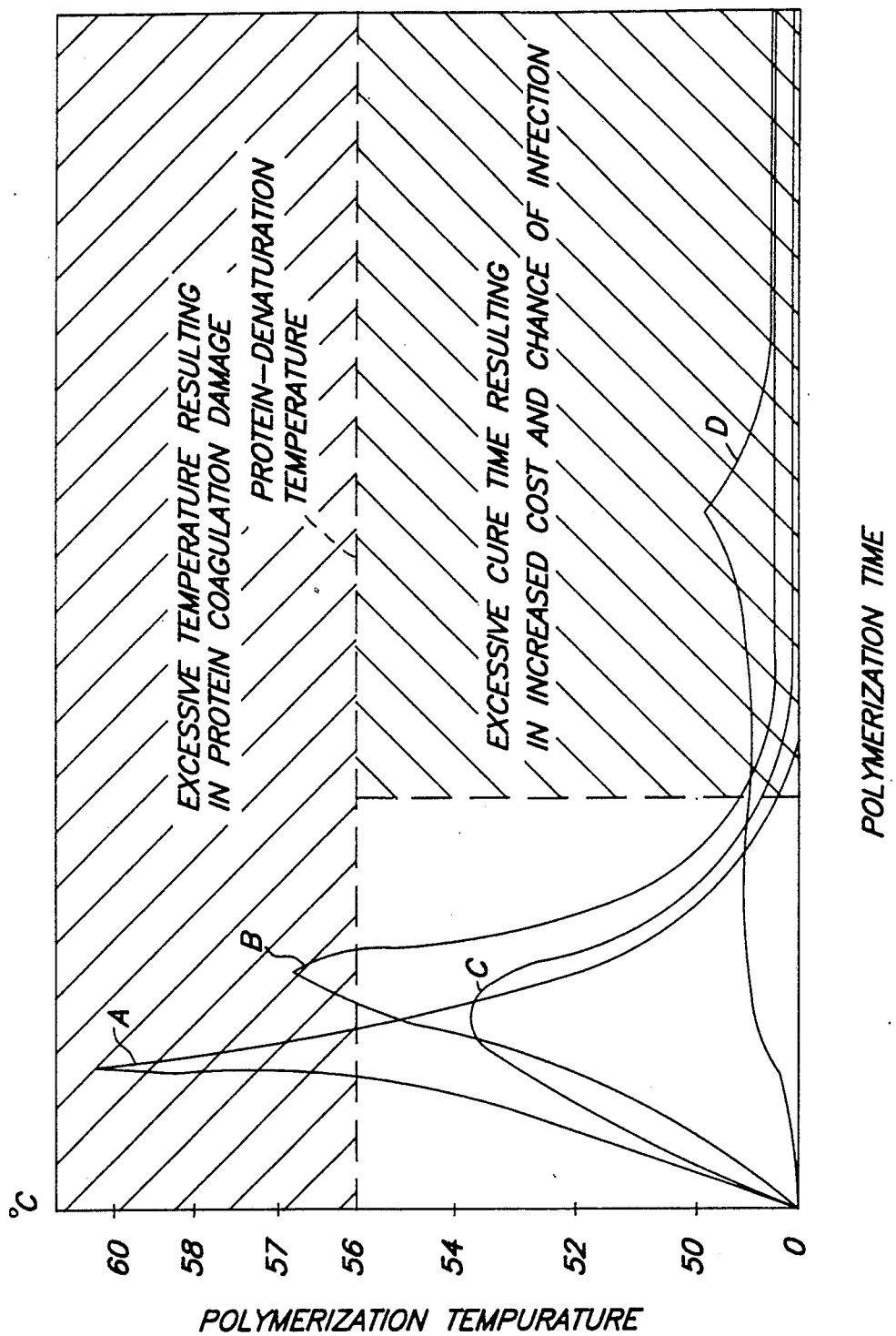
FIG. 2 is a graph illustrating polymerization temperature as a function of time for an unfilled bone cement, as well as bone cements filled with varying amounts of carbon fibers and/or apatite.

As can be seen from FIG. 2 and the foregoing Table, a bone cement comprised of polymethyl methacrylate containing 4% by weight of carbon fibers, i.e., composition A, will cure in an acceptably short period of time, but it exhibits a peak polymerization temperature of about 60° C., which can result in considerable protein coagulation damage. Similarly, a cement comprised solely of polymethyl methacrylate, i.e., composition B, cures in an acceptable period of time, but can still cause some heat damage because of its peak polymerization temperature of about 57° C. On the other, composition D, which contains 10% carbon fibers, but no apatite, exhibits a peak curing temperature of about 50° C., which is considerably below the critical protein-denaturation temperature, but it requires such a long time to cure that it is generally unacceptable for use as a bone cement. The only composition which exhibits both an acceptable polymerization time and peak polymerization temperature is composition C, i.e., a composition falling within the scope of the present invention.

Experiments have shown that, depending upon the intended purpose of the prosthesis, i.e., the age of the patient and the position in which the prosthesis is to be located, between 1 and 30% by weight of apatite produces good results, while the particle sizes may lie within a range of from 2 μm to 3 mm. Experiments have also shown that the use of from about 15 to about 25% apatite is preferred, and that the use of from about 2 to about 4% carbon fibers is preferred.

It may also be desirable to mix X-ray additives such as barium salts, with the cement and other natural minerals may usefully be added. Chemically produced apatite and apatite obtained from bones may also be used. It may, however, be expedient to utilize a mixture of calcium phosphates, so long as the resulting bone cement comprises at least about 1 to 30% apatite.

Bone cement with apatite admixed therewith may be made available in different forms. It is possible to use pure, conventional bone cement which is mixed with monomeric mixing fluid in a ratio suitable for the particular case, or for organic plastics material powder and the apatite to be provided in a predetermined ratio as a mixture, or for both constituents to be provided separately in powder form and then mixed to the required ratio.

To facilitate the insertion and use of the carbon fiber sock or stocking, it may expediently be fitted on a screw collar ring.

To charge the bone cement together with the carbon fiber stocking or sock into the marrow cavity of the bone, the stocking is preferably filled with bone cement and, in a damp state, is charged into the marrow cavity, the prosthesis shaft being subsequently forced home into the stocking.

Inasmuch as the present invention is subject to many variations, modifications and changes in detail, it is intended that all matter contained in the foregoing description or shown in the accompanying drawings shall be interpreted as illustrative and not in a limiting sense.

What is claimed is:

1. A bone cement for adhering a prosthetic device to a bone consisting essentially of polymethyl methacrylate or its derivatives, carbon fibers and an essentially non-absorbably mineral component in fine grained particle form, said essentially non-absorbably mineral component comprising apatite in an amount of between 1 and 301% by weight.

2. A bone cement according to claim 1, wherein said apatite is present in an amount between about 15 and 251% by weight.

3. A bone cement according to claim 1, wherein said carbon fibers are structured, said structure being provided by a linking method such as weaving, knitting or cross-linking by adhesion.

4. A bone cement according to claim 3, wherein said structured fibers are provided in the form of a tube, stocking or sock, the fibers being expediently distributed in the cement.

5. A bone cement according to claim 1, wherein said apatite is a mixture of synthetically produced apatite and apatite obtained from natural bone.

6. A bone cement according to claim 1, additionally containing an X-ray additive such as a barium salt.

7. A bone cement according to claim 1, additionally containing a mixture of essentially non-absorbably calcium phosphates.

* * * * *

UNITED STATES PATENT AND TRADEMARK OFFICE
CERTIFICATE OF CORRECTION

PATENT NO. : 5,049,157
DATED : September 17, 1991
INVENTOR(S) : MITTELMEIER ET AL.

It is certified that error appears in the above—identified patent and that said Letters Patent is hereby corrected as shown below:

Column 6, line 30, "non-absorbably" should be -- non-absorbable --;

Column 6, line 31, "non-absorbably" should be -- non-absorbable --;

Column 6, line 33, "301%" should be -- 30% --;

Column 6, line 36, "251%" should be -- 25% --; and

Column 6, line 51, "non-absorbably" should be -- non-absorbable --.

Signed and Sealed this

Twenty-seventh Day of April, 1993

*Attest:*

MICHAEL K. KIRK

*Attesting Officer*  *Acting Commissioner of Patents and Trademarks*